US00PP19519P2

(12) United States Plant Patent
Bradford

(10) Patent No.: US PP19,519 P2
(45) Date of Patent: Dec. 2, 2008

(54) INTERSPECIFIC TREE NAMED 'APRIPLUM III'

(50) Latin Name: ***Prunus* sp.**
Varietal Denomination: Apriplum III

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/984,898

(22) Filed: Nov. 26, 2007

(51) Int. Cl.
*A01H 5/00* (2006.01)

(52) U.S. Cl. ..... Plt./180
(58) Field of Classification Search ..... Plt./180
See application file for complete search history.

(56) References Cited

U.S. PATENT DOCUMENTS

PP7,504 P 4/1991 Bradford
PP14,247 P2 10/2003 Bradford

*Primary Examiner*—Annette H Para

(57) ABSTRACT

The present invention relates to an interspecific tree and more particularly to a new and distinct variety broadly characterized by a medium size, vigorous, hardy, and moderately productive tree. The variety produces a heavy bloom during the mid season with scant pollen and is self-unfruitful. The fruit matures under the ecological conditions described during early July, with first picking on Jul. 1, 2007. The fruit is uniformly small in size, nearly black in skin color, clingstone in type, globose in shape, a red and orange yellow two-tone in flesh color, firm and crisp in texture, and outstanding in flavor, having high sugar and a strong apricot presence.

1 Drawing Sheet

Botanical classification: *Prunus* sp.
Varietal denomination: 'Apriplum III'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Apriplum III'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2001 one tree of 'Black Noble' (U.S. Plant Pat. No. 7,504) plum was crossed by me in this manner. To pollinate this isolated tree, I selected bouquets from several sources of apricot and interspecific plum-apricot hybrid trees without keeping specific written details. Upon reaching maturity the fruit from this plum tree was harvested and the seeds were removed, cracked, stratified and germinated as a group with the label "H10P410". They were grown as seedlings on their own root in my greenhouse and upon reaching dormancy transplanted to a cultivated area of my experimental orchard located near Le Grand, Calif. in Merced County (San Joaquin Valley). During the summer of 2004 the claimed variety was selected by me as a single plant from the group of seedlings described above. Subsequent to origination of the present variety of interspecific tree. I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'Black Noble' (U.S. Plant Pat. No. 7,504) plum, by being self-unfruitful and by producing fruit that is similar in size, clingstone in type, nearly black in skin color, and very sweet, but is distinguished therefrom by producing very little pollen and by producing fruit that is a red and orange yellow two-tone rather than full red in flesh color, that has strong apricot flavor, and that matures about three weeks later.

SUMMARY OF VARIETY

The present interspecific variety is characterized by a medium size, vigorous, hardy, and moderately productive tree. Being self-unfruitful, the present variety requires cross pollination from an apricot, interspecific, or plum that blooms during the mid season. The present variety has a very heavy bloom but very light pollen production. This condition necessitates plenty of pollinators to be supplied in close proximity for normal production. The fruit matures under the ecological conditions described during early July, with first picking on Jul. 1, 2007. The fruit is uniformly small in size, nearly black in skin color, clingstone in type, globose in shape, a red and orange yellow two-tone in flesh color, firm and crisp in texture, and outstanding in flavor, having the very strong presence of apricot flavor balanced with high sugar.

DRAWING

The accompanying photograph consists of four whole fruits positioned to display the characteristics of the skin color and form, one fruit divided transversely to the suture plane to reveal the flesh and stone, a freshly cleaned stone, a young tip shoot growth, typical leaves, and two insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Jul. 14, 2007, on the original tree during its sixth growing season. The flower and bud descriptions were developed during the previous blooming season. All major color code designations are by reference to the Inter-Society Color Council, National Bureau of Standards. Common color names are also used occasionally.

Parentage

Seed parent: 'Red Noble' (U.S. Plant Pat. No. 7,504).
Pollen parent: Unknown.

Tree

Size: Medium, reaching and maintaining a height of 11' [3.35 m.] and a spread of 6' [1.83 m.] after six growing seasons utilizing typical dormant pruning.

Vigor: Moderately vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Central leader type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable mid seasonal blooming apricot, interspecific, or plum, such as 'August Yummy' (U.S. Plant Pat. No. 14,247) plum.

Bearing: Uncertain bearer, very dependent upon weather conditions during the blooming period.

Trunk:

*Size.*—Medium, reaching a maximum diameter of 4¼" [108 m.] after the sixth growing season.

*Texture.*—Shaggy.

*Bark color.*—A Moderate yellowish brown [77. m.yBr] and Dark grayish brown [62. d.gy.Br] variegation with Strong yellowish brown [74. s.yBr] crevices present.

*Lenticels.*—Approximate Number Per Square Inch: 6. Color: Brownish orange [54. brO]. Average Size: ¼" [6.4 mm.]. Shape: Eye-shaped, elongated.

Branches:

*Size.*—Diameter of lowest limb is 1¼" [32 mm.] measured 12" from central leader.

*Texture.*—Smooth on first and second year wood, increasing roughness with age.

*Color.*—1st Year Wood Topside: Moderate olive [107. m.Ol]. 1st Year Wood Underside: Strong yellow green [117. s.YG]. Older Wood: A Moderate brown [58. m.Br] and Brownish gray [64. brGy] variegation.

*Lenticels.*—Number Per Square Inch: More than 60 on second year wood. Color: Light yellowish brown [76. l.yBr]. Average Size: 1/64" [0.4 mm.]. Shape: Elongated, rectangular.

Leaves:

*Size.*—Medium. Average Length: 3¼" [83 mm.]. Average Width: 1⅝" [41 mm.].

*Arrangement.*—Alternate.

*Thickness.*—Medium.

*Form.*—Elliptical.

*Apex.*—Acuminate.

*Base.*—Rounded to somewhat acuminate with an average angle base angle of 75 degrees.

*Surface.*—Smooth.

*Color.*—Dorsal Surface: Moderate olive green [125. m.OlG]. Ventral Surface: Deep yellow green [118. deep YG].

*Margin.*—Finely serrate.

*Venation.*—Pinnately net veined.

*Petiole.*—Average Length: ¼" [6.4 mm.]. Average Thickness: 1/16" [1.6 mm.]. Color: Very yellow green [115. v.YG].

*Stipules.*—Number: 2 per leaf, up to 6 per growing tip. Average Length: 5/16" [7.9 mm.]. Color: Brilliant yellow green [116. brill.YG] becoming Moderate reddish brown [43. m.rBr] with age.

*Glands.*—Number: Mostly 2 per leaf. Position: Oppositely positioned at the intersection of the petiole and the leaf blade. Size: Small. Form: Globose. Color: Light yellow green [119. l.YG] becoming Deep reddish brown [41. deep rBr] in the center with age. Leaf buds: Pointed, medium.

Flower buds:

*Hardiness.*—Hardy, with respect to central California winters.

*Diameter.*—Typically 3/16" [4.8 mm.] 1 week before bloom.

*Length.*—Typically ⅜" [9.5 mm.] 1 week before bloom.

*Form.*—Not appressed.

*Surface.*—Pubescent.

*Tip color.*—White [263. White].

Flowers: Perfect, complete, perigynous, usually a single pistil, typically thirty or more stamens, five sepals and petal locations alternately positioned.

*Average flower diameter.*—1 1/16" [27.0].

*Number of petals.*—Five, no double blossoms observed.

*Petal shape.*—Oval to circular.

*Petal margin.*—Entire, smooth, wavy.

*Average petal diameter.*—½" [12.7 mm.].

*Average petal length.*—9/16" [14.3 mm.].

*Petal apex.*—Rounded.

*Petal base.*—Obtuse.

*Petal color.*—White [263. White] on both sides.

*Anther color.*—Pale yellow green [121. p.YG].

*Stigma color.*—Pale yellow green [121. p.YG].

*Sepal color.*—Strong yellow green [117. s.YG].

*Sepal length.*—5/32" [4.0 mm.].

*Sepal width.*—5/32" [4.0 mm.].

*Sepal apex.*—Rounded to elliptical to match the width and length.

*Sepal margin.*—Fairly smooth to the naked eye, slightly serrate when magnified.

*Average pistil length.*—3/8" [9.5 mm.], shorter than normal.
*Average stamen length.*—1/2" [12.7 mm.].
*Fragrance.*—Slight.
*Pollen production.*—Very light, not bee enticing.
*Blooming period.*—Medium, two days after 'Santa Rosa' plum (unpatented).
*Onset of bloom.*—One percent on Mar. 2, 2007.
*Date of full bloom.*—Mar. 9, 2007.
*Duration of bloom.*—One to two weeks, dependent on ambient temperature.
*Bloom density.*—Very heavy.
*Number per cluster.*—2 to 12, average 6.

FRUIT

Maturity when described: Firm ripe, Jul. 14, 2007.
Date of first picking: Jul. 1, 2007.
Date of last picking: Jul. 14, 2007.
Size: Uniform, small.
*Average diameter axially.*—2 1/16" [52.4 mm.].
*Average diameter across cheek plane.*—2 1/8" [54.0 mm.].
*Average diameter across suture plane.*—2 1/8" [54.0 mm.].
*Typical height.*—3.2 ounces [91 grams].
Form: Uniform, globose, symmetrical.
*Longitudinal section form.*—Mostly round.
*Transverse section through diameter.*—Round.
Suture: A distinct line located in a very shallow groove extending from the base to the apex.
Ventral surface: Rounded, slightly lipped toward the base.
Lips: Fairly equal.
Cavity: Flaring, circular, suture showing on one side, no stem markings present.
*Depth.*—1/4" [6.4 mm.].
*Breadth.*—7/16" [11.1 mm.].
Base: Somewhat truncate, cordate of viewed parallel to the suture.
Apex: Rounded.
Pistil point: An inconspicuous dot.
Stem: Medium.
*Average length.*—3/8" [9.5 mm.].
*Average width.*—5/64" [2.0 mm.].
Skin:
*Thickness.*—Medium.
*Surface.*—Smooth.
*Tenacity.*—Tenacious to the flesh.
*Astringency.*—Slight.
*Tendency to crack.*—Slight.
*Color.*—Blackish red [21. blackish R] with heavy Moderate orange yellow [71. m.OY] freckling throughout.
*Bloom.*—Abundant.
Flesh:
*Color.*—Very orange yellow [66. v.OY] toward the stone, Very deep red [14. v.deep R] toward the skin.
*Surface of pit cavity.*—Covered with Brilliant orange yellow [67. brill.OY] broken fibers when twisted from the stone.
*Amygdalin.*—Moderate.
*Juice.*—Abundant, rich.
*Texture.*—Firm, crisp.
*Fibers.*—Abundant, fine and tender.
*Ripens.*—Slightly earlier towards the apex.
*Flavor.*—Strong apricot presence, a tasty balance acid and abundant sugar, typically 25 brix.
*Aroma.*—Moderate.
*Eating quality.*—Outstanding.

STONE

Type: Clingstone.
Form: Oval.
Hilum: Narrow.
Base: Rounded.
Apex: Rounded to slightly acuminate, with a sharp 1/32" [0.8 mm.] tip.
Sides: Equal.
Surface: Rough throughout with a groove from base to apex on each side of the dorsal fin.
External color of stone: Dark orange yellow [72. d.OY].
Pit wall color when cracked: Moderate yellowish brown [77. m.yBr].
Cavity surface color: Light yellowish brown [76. l.yBr].
Average pit wall thickness: 1/16" [1.6 mm.].
Average width: 11/16" [17.5 mm.].
Average length: 15/16" [23.8 mm.].
Average breadth: 3/8" [9.5 mm.].
Tendency to split: None observed.
Kernel:
*Form.*—Oval.
*Skin color.*—Dark orange yellow [72. d.OY] when dried.
*Pellicle color.*—Moderate yellowish brown [77. m.yBr].
*Vein color.*—Strong yellowish brown [74. s.yBr].
*Taste.*—Bitter.
*Viable.*—Yes.
*Average width.*—3/8" [9.5 mm.].
*Average length.*—1/2" [12.7 mm.].
*Amygdalin.*—Moderate.

Use

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to its seed parent, 'Black Noble' (U.S. Plant Pat. No. 7,504) plum, by being self-unfruitful and by producing fruit that is similar in size, clingstone in type, nearly black in skin color, and very sweet, but is distinguished therefrom by producing very little pollen and by producing fruit that is a red and orange yellow two-tone rather than full red in flesh color, that has strong apricot flavor, and that matures about three weeks later.

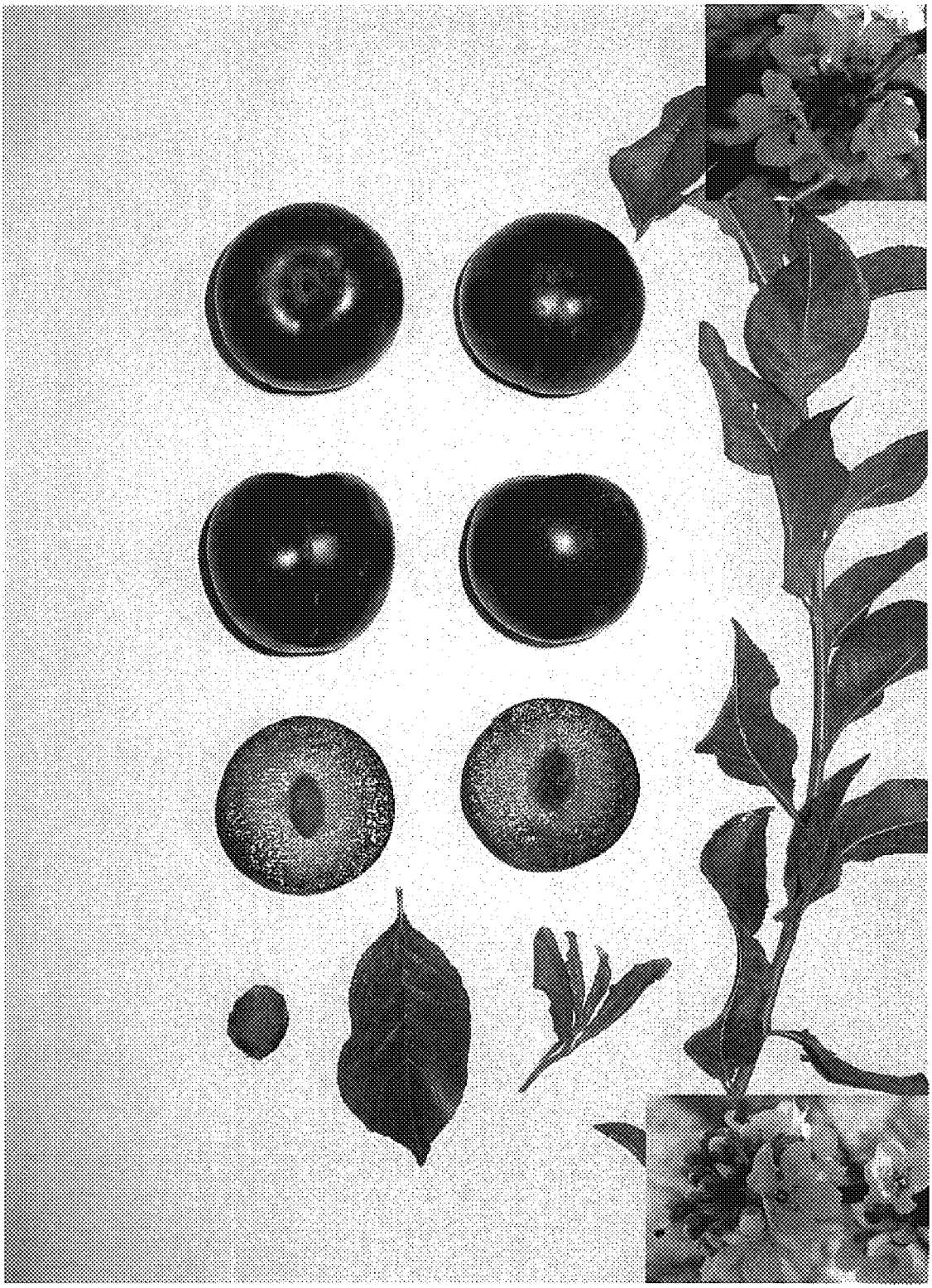

* * * * *